US00PP25647P2

(12) United States Plant Patent
Delabroye

(10) Patent No.: US PP25,647 P2
(45) Date of Patent: Jun. 23, 2015

(54) ***HEUCHERA* PLANT NAMED 'BROWN SUGAR'**

(50) Latin Name: ***Heuchera* hybrid**
Varietal Denomination: Brown Sugar

(71) Applicant: Sandrine Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 89 days.

(21) Appl. No.: 13/694,478

(22) Filed: Dec. 5, 2012

(51) Int. Cl.
*A01H 5/12* (2006.01)

(52) U.S. Cl.
USPC ..... Plt./440

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Phillips *Heuchera* Coral Bells—Alum Root—Fairy Flowers UC Master Gardener Handouts & Talks Business & Education Programs 2006-07 Sept-Cool Season Plants, 1 page.*

Piterek Garden—my passion! Nov. 30, 2011, retrieved on Aug. 6, 2014, retrieved from the Internet at <http://zurawki.blogspot.com/2011/11/heuchera-brown-sugar.html> 4 pp.*

Google English translation Ogrod—moja pasja! *Heuchera* 'Brown Sugar', 5 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Brown Sugar', characterized by its glossy leaves that are bronze in color with silver mottling, compact plant habit with a tight mound of foliage, its abundance of flowering stems, its medium pink flowers on dark brown-red flowering stems, its vigorous growth habit, and its tolerance to heat and humidity.

2 Drawing Sheets

Botanical classification: *Heuchera* hybrid.
Cultivar designation: 'Brown Sugar'.

CROSS REFERENCE TO A RELATED APPLICATION

This application is co-pending with a U.S. Plant Patent Application filed for a plant derived from the same breeding program that is entitled *Heuchera* Plant Named 'Vulcano' (U.S. Plant patent application Ser. No. 13/694,477).

BACKGROUND OF THE INVENTION

The present invention relates to a new and distinct cultivar of *Heuchera* of hybrid origin, botanically known as a *Heuchera* and is hereinafter referred to by its cultivar name 'Brown Sugar'.

The new cultivar arose from a cross made in 2008 by the Inventor in Hantay, France. An unnamed and unpatented proprietary hybrid plant of *Heuchera sanguinea* was used as the male parent. The Inventor selected 'Brown Sugar' in 2010 as a single unique plant amongst the seedlings that resulted from the above crosses.

Asexual propagation of the new cultivar was first accomplished by the Inventor by division in Hantay, France in 2011. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Brown Sugar' as a new and unique cultivar of *Heuchera*.

1. 'Brown Sugar' exhibits glossy leaves that are bronze in color with silver mottling in spring and becoming more green when mature.
2. 'Brown Sugar' exhibits a compact plant habit with a tight mound of foliage.
3. 'Brown Sugar' exhibits an abundance of flowering stems.
4. 'Brown Sugar' exhibits medium pink flowers on dark brown-red flowering stems.
5. 'Brown Sugar' exhibits a vigorous growth habit.
6. 'Brown Sugar' exhibits a tolerance to heat and humidity.

'Brown Sugar' is a unique *Heuchera* with foliage coloration that is unknown to exist in other cultivars of *Heuchera* known to the Inventor. The female parent differs from 'Brown Sugar' in having foliage that is green in color and lacks any bronze coloration. The male parent, 'Beaujolais', differs from 'Brown Sugar' in having foliage that is dark burgundy red in color with a silver overlay and in being less floriferous. 'Brown Sugar' can also be most closely compared to the cultivars: 'Vulcano', 'Crème Brulee' (not patented) and 'Bronze Beauty' (not patented) for its similarity in foliage coloration and in having *Heuchera×villosa* in its parentage. 'Vulcano' differs from 'Brown Sugar' in having foliage that is amber in color and in being less floriferous with darker pink flowers. 'Crème Brulee' differs from 'Brown Sugar' in having more ruffled foliage that is peachy orange in summer and becomes brown in cold temperatures, and in having creamy white flowers. 'Bronze Beauty' differs from 'Brown Sugar' in having much larger leaves that are very pubescent and lacking silver mottling and in having creamy white flowers.

BRIEF DESCRIPTION OF THE DRAWING

The accompanying colored photographs illustrate the overall appearance and distinct characteristics of the new *Heuchera*. The photographs were taken of a plant two years in age as grown outdoors in a 7.5-liter container.

The photograph in FIG. 1 provides a side view of the plant habit of 'Brown Sugar' in bloom.

Figure 1:
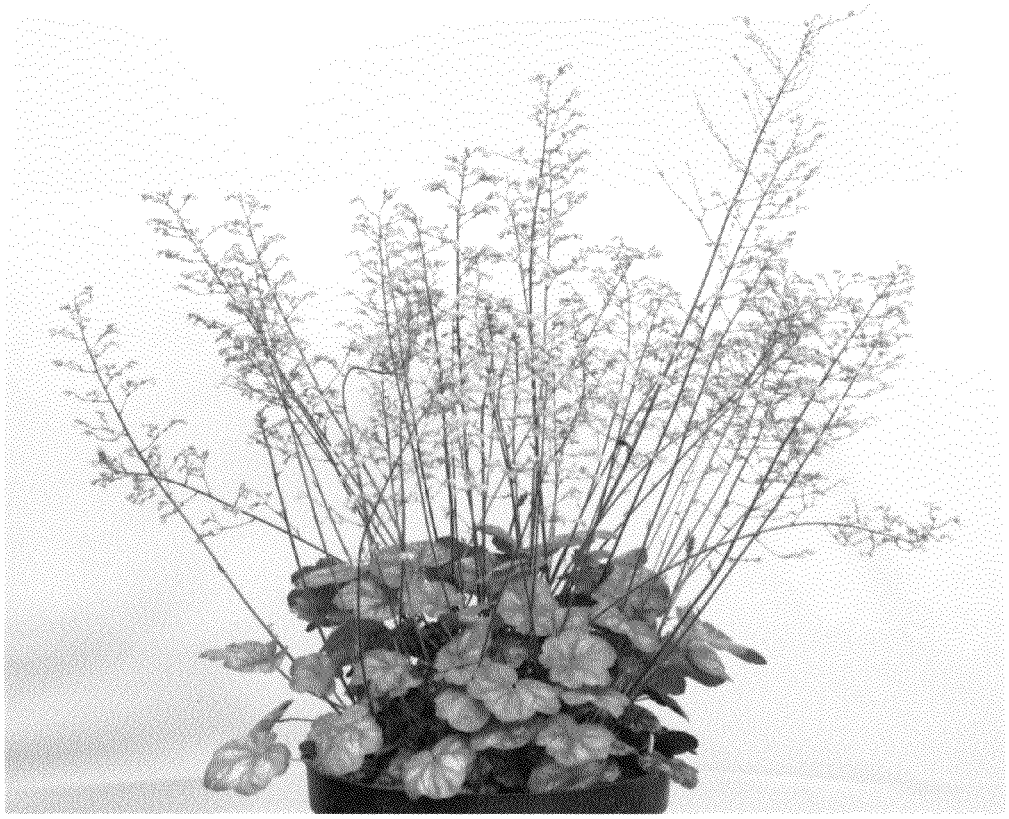
Figure 2:
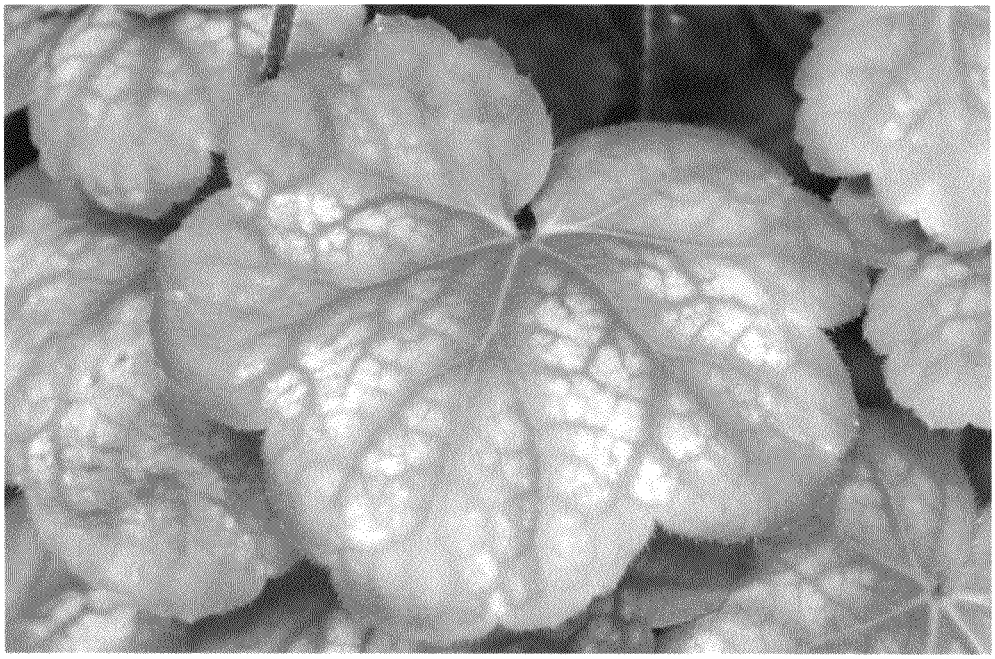

The photograph in FIG. 2 provides a close-up view of a leaf of 'Brown Sugar'.

Figure 3:
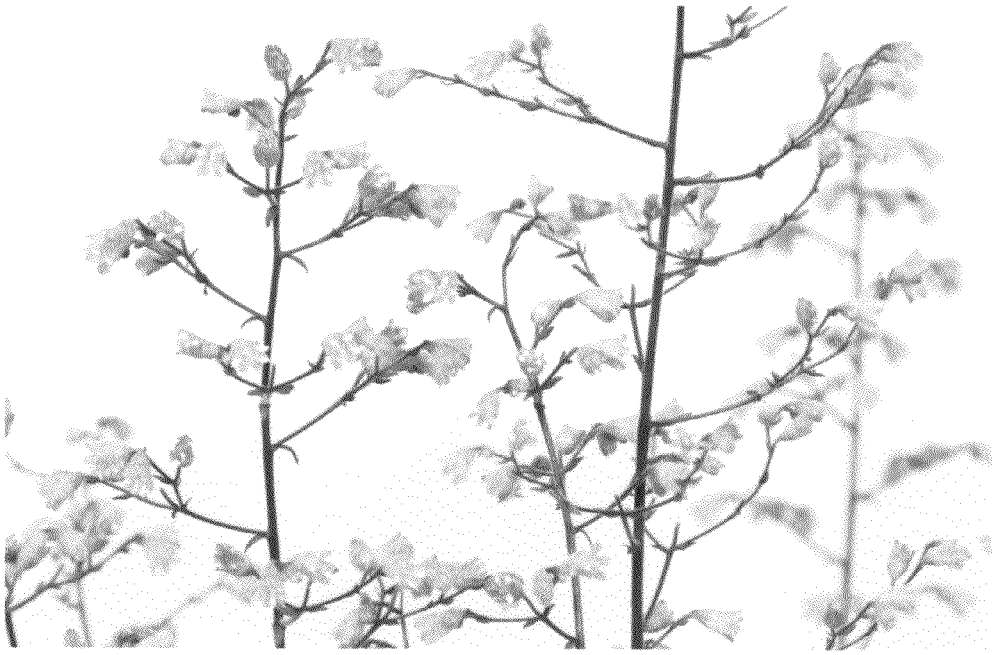

The photograph in FIG. 3 provides a close-up view of the flowers of 'Brown Sugar'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year old plants of the new cultivar as grown outdoors in 7.5-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early spring-spring in The Netherlands.

*Plant type.*—Herbaceous perennial.

*Plant habit.*—Compact, clump-forming, mounded foliage.

*Height and spread.*—Average of 20.5 cm in height from soil to top of leaves, 58.6 cm from soil to top of inflorescences, and about 62.5 cm in width.

*Hardiness.*—At least in U.S.D.A. Zones 3 to 8.

*Diseases and pests.*—Not more susceptible to pests and diseases than other *Heuchera* varieties.

*Environmental stresses.*—Tolerant to heat and humidity.

*Root description.*—Fibrous roots on woody rootstalks.

*Branching habit.*—Flowering stem emerge from basal rosettes, no lateral branches.

*Propagation.*—In vitro propagation is the preferred method, division are also possible.

*Growth rate.*—Vigorous.

Stem description (flowering stem or main peduncle):

*Shape.*—Round.

*Stem color.*—177A.

*Stem size.*—An average of 2 mm in diameter and 31.5 cm in length (including rachis).

*Stem strength.*—Strong.

*Stem aspect.*—Flowering stems grow in an average angle of 60° to base (0°=horizontal).

*Stem surface.*—Moderately glossy, rounded, densely covered with short hairs, average of 1 mm in length, NN155D in color.

*Stem number.*—Average of 54 flowering stems.

Foliage description:

*Leaf shape.*—Orbicular.

*Leaf division.*—Simple.

*Leaf base.*—Hastate.

*Leaf apex.*—Mucronulate.

*Leaf venation.*—Laciniate.

*Leaf margins.*—Lobed with average of 7 lobes per leaf, lobe margins crenate, main veins on underside sparsely covered with short hairs 1 mm in length and NN155D in color.

*Leaf attachment.*—Petiolate.

*Leaf arrangement.*—Alternate, basal rosettes.

*Leaf orientation.*—Typically nearly horizontal to petiole and slightly cupped.

*Leaf surface.*—Both surfaces dull and smooth, some sparse pubescence on main veins on lower surface.

*Leaf color.*—Young upper surface; 199D mottled with 156A, veins and margins N199C, changing to 195B, with veins and margins 152A, young lower surface; 184B, mature upper surface; 198B, margins and area near the veins between 147A and 189A, mature lower surface; N77C.

*Leaf size.*—Average of 6.4 cm in length and 6.7 cm in width.

*Leaf quantity.*—15 per basal rosette.

*Petioles.*—Round in shape, average of 10.6 cm in length and 2 mm in width, 177B in color, slightly pubescent surface.

*Stipules.*—Small leafy stipules at the base of each leaf, narrow acute apex, with an average of 1.2 cm in length and 3 mm in width and 70B in color.

Flower description:

*Inflorescence type.*—Numerous small bell-shaped flowers arranged on pyramidal panicles on flower scapes emerging from the base of the rosette.

*Inflorescence size.*—An average of 18.1 cm in height (excluding peduncle) and about 7.6 cm in width.

*Inflorescence number.*—An average of 54 per 7.5-liter container.

*Flower fragrance.*—None.

*Flower quantity.*—Average of 60 flowers per flowering stem.

*Flower lastingness.*—Average of one week.

*Flower buds.*—Oblong in shape, an average of 5 mm in diameter and 6 mm in depth, N57C in color with base 58D.

*Flower aspect.*—Drooping to outward.

*Flower type.*—Campanulate.

*Flower size.*—About 4 mm in length and 2 mm in diameter.

*Petals.*—About 5, rotate arrangement and implanted in the hypanthium at base, linear in shape, margin is entire, apex is narrowly acute, upper and lower surface is dull and smooth, color of upper and lower surface when opening and mature is 69D, about 2.5 mm in length and 0.8 mm in width.

*Calyx.*—Campanulate, sepals fused to hypanthium, 5 mm in depth and 6 mm in diameter.

*Sepals.*—5, fused, campanulate hypanthium, elliptic in shape, about 5 mm in length and 2 mm in width, margin is entire, apex is broadly acute, fused base, surface is moderately covered with very short glandular hairs about 0.5 mm in length and NN155D in color, color: immature upper and lower surface; 58C, base 58D, mature upper and lower surface; 61D, base 68B to 68C.

*Bracts.*—1, at base of secondary peduncle and petioles, lanceolate in shape, 187B in color, about 6 mm in length and 1 mm in width, acute apex, base truncate.

*Peduncles.*—Rachis; average of 16.6 cm in length and 1.5 mm in width, moderate strength, held at a 0° angle (straight on top of flowering stem), color of both surfaces; N186C, secondary peduncles; average of 1.9 cm in length, 0.75 mm in diameter, moderate in strength, held at a 60° (0°=straight upright) to rachis color of both surfaces; N186C, surfaces moderately glossy, rounded, densely covered with short hairs, average of 1 mm in length, NN155D in color.

*Pedicels.*—Average of 2 mm in length and 0.5 mm in width, color 187B, pedicel of primary flower of each spikelet straight on top of secondary pedicel, pedicels of secondary and tertiary flowers of each spikelet in an average angle of 45° (0°=straight on top of secondary peduncle), surface moderately glossy, rounded, densely covered with short hairs, average of 1 mm in length, NN155D in color.

Reproductive organs:

*Gynoecium.*—2 pistils, pointed in shape, about 3 mm in length, and N155D in color, styles are about 2.75 mm in length and about NN155D in color, ovaries are 145C in color.

*Androcoecium.*—About 5 stamens, anthers are ovate in shape, about 0.25 mm in length and 201D in color, filament 2 mm in length and N155B in color, pollen is moderate in quantity and 156D in color.

*Seed/fruit.*—No fruit or seeds detected to date.

It is claimed:

1. A new and distinct cultivar of hybrid *Heuchera* plant named 'Brown Sugar' as herein illustrated and described.

* * * * *